United States Patent [19]

Bisso et al.

[11] Patent Number: 5,039,330

[45] Date of Patent: Aug. 13, 1991

[54] USE OF FRUCTOSE-1,6-DIPHOSPHATE IN BOTANY AS GERMINATION AND PLANT GROWTH PROMOTER

[75] Inventors: Guillermo M. Bisso; Franco Gitti, both of Rome, Italy

[73] Assignee: Biomedica Foscama Industria Chimico-Farmaceutica S.p.A., Rome, Italy

[21] Appl. No.: 489,223

[22] Filed: Mar. 6, 1990

[30] Foreign Application Priority Data

Mar. 10, 1989 [IT] Italy ............................... 19729 A/89

[51] Int. Cl.$^5$ ............................................ A01N 43/08
[52] U.S. Cl. ............................................ 71/77; 71/86; 536/1.1; 536/117
[58] Field of Search ........................ 71/77, 86, 88, 89; 536/1.1, 117

[56] References Cited

U.S. PATENT DOCUMENTS 3,066,135 11/1962 Baruchello ........................ 260/234
4,546,095 10/1985 Markov ................................ 514/23
4,576,930 3/1986 Sugiyama et al. .................... 514/23

OTHER PUBLICATIONS

"Development and Properties of Fructose 1,6-Bisphosphatase in the Endosperm of Castor-Bean Seedlings", Youle et al., Biochem. J. (1976) 154, 647–652.

Primary Examiner—Richard L. Raymond
Assistant Examiner—Brian M. Burn
Attorney, Agent, or Firm—Walter H. Schneider

[57] ABSTRACT

The invention concerns the use of fructose-1,6-diphosphate in botany for the formulations of compositions suited for the stimulation of the germination of dormant seeds and of the growth of stem tissues of growing plants.

5 Claims, No Drawings

USE OF FRUCTOSE-1,6-DIPHOSPHATE IN BOTANY AS GERMINATION AND PLANT GROWTH PROMOTER

The present invention refers to the use of fructose-1,6-diphosphate in agriculture soils to promote the germination of dormant seeds and to stimulate the tissue growth in the stem of plants in the growth phase.

Auxins, being able to stimulate the growth by cell enlargement as well as cytokinins, being able to stimulate the germination of dormant seeds, are well known.

In the first case, one of the interpretations suggested to explain the mechanism of action of the phytohormon is that the latter, acting on the cell metabolism, promotes the release of protons from the cytoplasm, first by extrusion at the cell wall and then by diffusion to the external medium. The resulting decrease of the wall pH would cause a marked increase of the cell enlargement since the latter is the consequence of the plastic extensibility of the wall, property which is known to be pH-dependent.

On the other hand, as far as the stimulation of the germination in quiescent seeds is concerned, even though the active phytohormones are of a different kind (cytokinins and gibberellins) it is current opinion that their mechanism of action at the wall membrane is similar to that of auxins. One of the recurring hypothesis is that they cause an increase in the water absorption by the seed and this would result in an activation of the protein synthesis. Moreover some researchers have shown an increase of $K^+$ ions as a consequence of the action of some of these phytohormones. The fructose-1,6-diphosphate (FDP) has been used for many years in human therapy with remarkable success, particularly in the cardiological field because of its marked protective action on the myocardium in patients affected by different cardiac diseases.

Now, from the clinical trials and from "in vitro" and "in vivo" experimental data on animals it was deduced that FDP, interacting with the cell membrane, changes the ionic permeability thereof making the release of protons from the cytoplasm easier with the consequent increase of the intracellular pH. The phosphofructokinase, the carbohydrate and the ATP metabolism are therefore activated.

It has now been found that FDP is able to stimulate the germination of dormant seeds and the growth of the stem tissues in growing plants. This property of FDP, never recognized previously, has been confirmed in the Applicant's research laboratories by several tests, some results of which will be hereinafter reported.

Research carried out in comparison with known phytohormones on different kinds of dormant seeds have shown that FDP induces the germination of said seeds with equal or greater effectiveness then known phytohormones (gibberellic acid, benzyladenine).

This effectiveness was noticed not only from the germination rate but also from the concentration of the known phytohormones. Further experiments on the cell enlargement in comparison with some auxins have shown that the stimulating action of FDP is comparable with that of used auxins (indolyl-3-acetic acid).

From a practical point of view, FDP may be used in liquid or solid formulations to be applied to the sown soil or to the leaves of the growing plant. According to the present invention, the FDP containing formulations may contain soluble salts of FDP such as sodium salts ($FDPH_2Na_2$, $FDPH_3Na$); potassium salts ($FDPH_2K_2$, $FDPHK_3$, $FDPK_4$); calcium salt ($FDPH_2Ca$); magnesium salt ($FDPH_2Mg$) or insoluble salts as zinc salt ($FDPZn_2$); iron salts ($FDPHFe$, $FDPH_2Fe$).

In said formulations, a certain effective amount of the chosen FDP salt is added with an inert compound so as to allow a suitable application to the soil or to the plant to be treated.

They include liquid formulations (aqueous solutions or emulsifiable liquid concentrates) and solid formulations (powders, granules or wettable powders). The liquid formulations, namely the aqueous solutions, prepared with the soluble salts and the emulsifiable concentrates, allowing also the use of insoluble salts, are particularly preferred for their ease of use.

These emulsifiable concentrates may be suitably diluted in water or oil at the desired concentration of FDP, obtaining stable emulsions which are then sprayed on soil or leaves. In the case of application to the soil, solid formulations (particularly when insoluble iron or zinc salts are used) may also be used.

In both cases, formulations containing from 1 to 1000 ppm of a FDP salts proved to be effective according to the present invention.

Typical formulations of the invention are the following:

| a) | Emusifiable concentrate: | |
|---|---|---|
| | FDP salt | 20 |
| | Sodium dodecylsulfate | 2 |
| | Octylphenoxy-polyethoxy ethanol | 3 |
| | Kerosene | 75 |
| b) | Fluid liquid concentrate: | |
| | FDP salt | 35.0 |
| | Colloidal magnesium silicate | 0.5 |
| | Sodium alkylnaphthalenesulfonate | 2.5 |
| | Propylenglycol | 7.0 |
| | Paraformaldehyde | 0.2 |
| | Water | 54.8 |

Both concentrates are dispersed in water at the desired concentration of FDP in order to be sprayed on the soil or leaves.

| c) | Wettable powders | |
|---|---|---|
| | FDP salt | 50 |
| | Inert carrier (talc, kaolin, bentonite, diatomaceous earth) | 45 |
| | Sodium dodecyl sulfate | 2.5 |
| | Octyl phenoxy polyethoxy ethanol | 2. |

This powder is dispersed in water at the desired concentration of FDP and the obtained liquid suspension is sprayed on the soil or leaves.

| d) | Powder | |
|---|---|---|
| | FDP salt | 15 |
| | Inert carrier (talc, bentonite, diatomaceous earth, kaolin) | 85 |

This powder is used as such or after granulation preferably for the treatment of sown soils.

The invention is now illustrated by the following examples.

EXAMPLE 1

Wheat seeds (Triticum durum D, c.v. Cappelli) were germinated in the dark at 25° C. in Petri dishes containing filter paper disks soaked in distilled water or in a 15 mM fructose-1,6-diphosphate sodium salt. A 0.2 M gibberellic acid solution in 0.002N KOH adjusted to pH 6.0 with 0.1N HCl was used as a control. 100 seeds were used for each dish and each test was carried out in duplicate. The germination was considered to have taken place when the root protrusion was evident. Seeds stored after the harvest for 2 different periods of time were used: 6 months (1986) and 18 months (1985). The count of the germinated seeds was carried out after incubation at 25° C. for 24 hours. The tests were carried out in January 1987.

TABLE I

EFFECT OF FRUCTOSE-1,6-DIPHOSPHATE SODIUM SALT ON THE GERMINATION OF WHEAT SEEDS

| TREATMENT | % GERMINATION (1) | |
|---|---|---|
| | 1985 HARVEST | 1986 HARVEST |
| FDP (15 mn) | 69 ± 4 | 51 ± 5 |
| Gibbelleric acid (200 mn) | 65 ± 5 | 45 ± 6 |
| H$_2$O | 48 ± 7 | 10 ± 2 |

(1) Means ± SD of 5 different tests carried out in duplicate.

EXAMPLE 2

Lettuce seed (Lactuca sativa, C.V. grand Rapids) were germinated in the dark at 25° C. after irradiation for 30' with white light in Petri dishes containing filter paper disks soaked with distilled water or in a 15 mM fructose-1,6-diphosphate sodium salt solution. A 0.1 M N-6-benzyladenine solution in 0.002N KOH adjusted to pH 6 was used as control. 100 seeds were used for each dish and each test was carried out in duplicate.

The germination was checked at different intervals (16, 24, 32, 40 and 48 incubation hours) and was considered to have taken place when the root protrusion was clearly evident. Table 2 shows the percentage of germinated seeds (mean±standard deviation) corresponding to 5 tests carried out in duplicate.

TABLE II

EFFECTS OF FRUCTOSE-1,6-DIPHOSPHATE ON SEED GERMINATIONS

| INC. TIME (HOURS) | % GERMINATION | | | | |
|---|---|---|---|---|---|
| | 16 | 24 | 32 | 40 | 48 |
| H$_2$O | 5% ± 0.5 | 8% ± 1.0 | 28% ± 2.0 | 45% ± 5 | 65% ± 4.5 |
| FDP (15 mM) | 15% ± 1.5 | 35% ± 2.0 | 65% ± 3.5 | 85% ± 5.5 | 90% ± 7 |
| BA (100 mM) | 8% ± 1.0 | 15% ± 0.8 | 40% ± 3.0 | 60% ± 4.0 | 83% ± 6.5 |

EXAMPLE 3

Pea seeds (Pisum sativum, c.v. Alaska) were incubated at 25° C. in the dark for a week; after germination, segments of about 10–15 mm were cut from the growing side of the distal internode. Randomized batches of 20 segments, thoroughly washed with distilled water, were incubated with 10 ml of distilled water at room temperature until the pH of the medium was stabilized to 6.5; a fructose-1,6-diphosphate solution was then added so as to have a final concentration of 15 mM continuing the incubation at room temperatures for further 3 hours.

The percent weight increase was then evaluated, calculated with respect to the wet weight of the segments at the end of preincubation.

Indolyl-3-acetic acid at the final concentrations of 0.01 mM was used as control growth-promoter.

TABLE III

EFFECTS OF FRUCTOSE-1,6-DIPHOSPHATE ON THE WET WEIGHT INCREASE IN THE PEA INTERNODE TEST

| | % WEIGHT INCREASE OF SEGMENTS (1) |
|---|---|
| CONTROL (distilled water) | 5.7 ± 0.9 |
| FDP (15 mM) | 31.9 ± 1.3 |
| IAA (10 mM) | 20.2 ± 2.4 |

(1) Means ± standard deviation in 5 different tests.

We claim:

1. A method of promoting the germination of dormant seeds and the growth of stem tissues of growing plants which comprises applying thereto an effective amount of a salt of fructose-1,6-diphosphate in admixture with an inert carrier.

2. A method according to claim 1 in which said salt is a water-soluble salt selected from the group consisting of sodium, potassium, calcium and magnesium salts.

3. A method according to claim 1 which said salt is a water-insoluble salt selected from zinc and iron salts.

4. A method according to claim 2 wherein the salt of fructose-1,6-diphosphate is in the form of an aqueous solution.

5. A method according to claim 4 wherein the salt of fructose-1,6-diphosphate is in a form selected from emulsions and solids.

* * * * *

UNITED STATES PATENT AND TRADEMARK OFFICE
CERTIFICATE OF CORRECTION

PATENT NO. : 5,039,330

DATED : August 13,1991

INVENTOR(S) : Guillermo M. Bisso; Franco Gritti

It is certified that error appears in the above-identified patent and that said Letters Patent is hereby corrected as shown below:

On the Title page, Item [75], the name "Franco Gitti"

should read---Franco Gritti---.

Signed and Sealed this

Ninth Day of February, 1993

Attest:

STEPHEN G. KUNIN

*Attesting Officer*  Acting Commissioner of Patents and Trademarks